(12) United States Patent
Misumi et al.

(10) Patent No.: US 9,436,084 B2
(45) Date of Patent: Sep. 6, 2016

(54) POSITIVE-WORKING PHOTORESIST COMPOSITION FOR THICK FILM FORMATION

(75) Inventors: Koichi Misumi, Kawasaki (JP); Toshiki Okui, Kawasaki (JP)

(73) Assignee: TOKYO OHKA KOGYO CO., LTD., Kanagawa (JP)

( * ) Notice: Subject to any disclaimer, the term of this patent is extended or adjusted under 35 U.S.C. 154(b) by 951 days.

(21) Appl. No.: 11/792,752

(22) PCT Filed: Mar. 22, 2006

(86) PCT No.: PCT/JP2006/306389
§ 371 (c)(1),
(2), (4) Date: Jun. 11, 2007

(87) PCT Pub. No.: WO2006/101250
PCT Pub. Date: Sep. 28, 2006

(65) Prior Publication Data
US 2008/0026321 A1    Jan. 31, 2008

(30) Foreign Application Priority Data
Mar. 23, 2005   (JP) .................................. 2005-084827

(51) Int. Cl.
| | | |
|---|---|---|
| *G03F 7/004* | (2006.01) | |
| *G03F 7/039* | (2006.01) | |
| *H01L 21/027* | (2006.01) | |
| *C08F 220/18* | (2006.01) | |
| *C07D 251/02* | (2006.01) | |

(52) U.S. Cl.
CPC ........... *G03F 7/0397* (2013.01); *C07D 251/02* (2013.01); *C08F 220/18* (2013.01); *G03F 7/004* (2013.01); *G03F 7/0392* (2013.01); *H01L 21/0274* (2013.01)

(58) Field of Classification Search
USPC .................................................... 430/270.1
See application file for complete search history.

(56) References Cited

U.S. PATENT DOCUMENTS

| | | | |
|---|---|---|---|
| 5,403,695 A | 4/1995 | Hayase et al. | |
| 6,517,992 B1 * | 2/2003 | Wang et al. ............... | 430/270.1 |
| 6,933,094 B2 * | 8/2005 | Miyaji et al. .............. | 430/270.1 |
| 2002/0115018 A1 * | 8/2002 | Hatakeyama et al. ..... | 430/270.1 |
| 2004/0038148 A1 * | 2/2004 | Ohta et al. ................. | 430/270.1 |
| 2005/0266336 A1 * | 12/2005 | Kodama .................... | 430/270.1 |
| 2006/0040203 A1 * | 2/2006 | Kodama et al. ........... | 430/270.1 |
| 2006/0141386 A1 * | 6/2006 | Okui et al. ................. | 430/270.1 |
| 2006/0210919 A1 * | 9/2006 | Mizutani et al. .......... | 430/270.1 |
| 2007/0003871 A1 * | 1/2007 | Kodama et al. ........... | 430/270.1 |

FOREIGN PATENT DOCUMENTS

| | | |
|---|---|---|
| JP | 2001-281862 | 10/2001 |
| JP | 2002-196497 | 7/2002 |
| JP | 2004-309775 | 11/2004 |
| JP | 2004-309776 | 11/2004 |
| JP | 2004-309778 | 11/2004 |
| KR | 10-2004-0029977 | 4/2004 |
| WO | 02/093262 | 11/2002 |

OTHER PUBLICATIONS

Korean Office Action dated Jul. 28, 2008 issued in connection with Korean Application No. 10-2007-7024201 (with partial English language translation).

* cited by examiner

*Primary Examiner* — Amanda C Walke
(74) *Attorney, Agent, or Firm* — Wenderoth, Lind & Ponack, L.L.P.

(57) ABSTRACT

The invention provides a chemical-amplification positive-working photoresist composition suitable for forming a resist film of a relatively large thickness on a substrate in addition to other advantages. The inventive composition contains (A) a photoacid-generating agent, (B) an alkali-insoluble resin capable of being imparted with increased alkali-solubility by interaction with an acid, (C) an alkali-soluble resin and (D) an organic solvent, wherein the component (C) is ($C_1$) a polyhydroxystyrene or a copolymer having at least 80% by mass of the hydroxystyrene units in an amount not exceeding 15 parts by mass relative to 100 parts by mass of the total amount of the components (B) and (C).

5 Claims, No Drawings

US 9,436,084 B2

POSITIVE-WORKING PHOTORESIST COMPOSITION FOR THICK FILM FORMATION

TECHNICAL FIELD

The present invention relates to a chemical-amplification positive-working photoresist composition suitable for forming a resist film of a large thickness on a substrate.

BACKGROUND ART

Many of the electronic devices constituting a variety of electronic appliances are usually manufactured by utilizing the photolithographic technology with the use of a photosensitive resin composition of which the major current in recent years is with the so-called chemical-amplification positive-working photoresist compositions.

It is a recent trend in the field of manufacturing a variety of electronic devices requiring fine working as represented by semiconductor devices that the devices have acquired more and more increased density and degree of integration. This trend leads to an increased demand for the chemical-amplification positive-working photoresist compositions capable of complying therewith.

Along with the trend toward increased fineness in electronic devices, LSIs are required to be of a higher degree of integration and assemblage of such an LSI into an electronic appliance is conducted by way of the multiple-pin thin-film mounting process such as the tape-automated bonding process and the flip-chip process having made their debut.

It is a requirement in the aforementioned multiple-pin thin-film mounting process that protruded electrodes of a 10 μm or larger height or so-called bumps are provided as the connecting terminals on the circuit board. While the bumps are formed in a process in which a barrier metal is stratified on the circuit board bearing an LSI device, a resist film formed thereon is exposed to actinic rays through a photomask of such a pattern as to open the resist film in the points corresponding to the bumps followed by development to give a replica mold which is subjected to plating with an electrode material such as gold and copper followed by removal of the worn-out resist composition and barrier metal, the resist composition used in this process is required to be suitable for the formation of a coating film having a uniform thickness of 20 μm or larger.

In view of the higher density as compared with the cases of the traditional positive-working photosensitive resin compositions containing a quinonediazide compound, on the other hand, it is only in recent years that the chemical-amplification photoresist compositions are highlighted, of which the principal ingredients include a resin capable of changing the solubility in an alkaline solution by interacting with an acid and a photoacid-generating agent capable of generating an acid by irradiation with actinic rays and these resist compositions are also in the major current as a resist composition for the preparation of electronic devices provided with the aforementioned bumps. Accordingly, the demand is increasing for a chemical-amplification positive-working photoresist composition suitable for the formation of a resist film of a large film thickness necessary for bump formation.

Several proposals have been made in this regard including a positive-working radiation-sensitive resin composition for preparation of plated articles containing a photoacid generating agent, a polymer having recurring units represented by the general formula

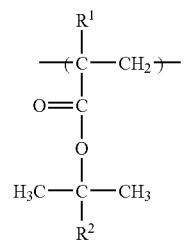

(in the formula, $R^1$ is a hydrogen atom or a methyl group and $R^2$ is an optionally substituted cycloalkyl group or aryl group having 6 to 20 carbon atoms)
and an organic solvent (see JP2001-281862A), a chemical-amplification positive-working photoresist composition for large film thickness containing a photoacid generating agent, a copolymer containing the structural units represented by the general formula

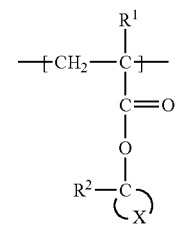

(in the formula, $R^1$ is a hydrogen atom or a methyl group, $R^2$ is a lower alkyl group and X is a group capable of forming a hydrocarbon ring of 5 to 20 carbon atoms together with the carbon atom to which the same is bonded)
and an alkali-soluble resin (see JP2004-309775A), a chemical-amplification positive-working photoresist composition for large film thickness containing a photoacid generating agent, a copolymer containing the structural units represented by the general formula

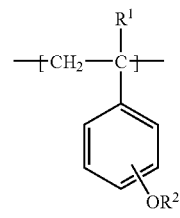

(in the formula, $R^1$ is a hydrogen atom or a methyl group and $R^2$ is an acid-labile group)
and an alkali-soluble resin (see JP2004-309776A), a chemical-amplification positive-working photoresist composition for large film thickness containing a photoacid generating agent, and a copolymer containing the structural units represented by the general formula

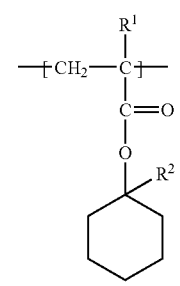

(in the formula, R¹ is a hydrogen atom or a methyl group and R² is a lower alkyl group) (see JP2004-309778A) and elsewhere.

It is, however, a difficult matter to decrease the defects of the chemical-amplification positive-working photoresist compositions described in the above-cited four patent documents relative to the higher performance required in the current photoresist compositions including the coating adaptability, peelability, development velocity and patterning fidelity as well as the coating adaptability for a large film thickness.

DISCLOSURE OF THE INVENTION

The object of the present invention is to provide a chemical-amplification positive-working photoresist composition capable of overcoming the defects in conventional chemical-amplification positive-working photoresist compositions for large film thickness having good coating adaptability and peelability, having a large development velocity without the trouble by dissolving of the resist layer in the unexposed areas during development and capable of giving a high-fidelity pattern still without decreasing the coating adaptability even in the formation of a large-thickness resist film.

The inventors have continued extensive investigations in order to develop a chemical-amplification positive-working photoresist composition having excellent properties suitable for the formation of a large thickness film to arrive at a discovery that, in a chemical-amplification positive-working photoresist composition containing a photoacid generating agent, alkali-insoluble resin capable of being imparted with an increased alkali-solubility by interacting with an acid and an organic solvent, the object can be accomplished by using a resin containing a large amount of hydroxystyrene units as the alkali-soluble resin for improving the coating adaptability in coating for a large thickness film formation and dissolvability in development and peeling and by controlling the mass proportion of the resin containing hydroxystyrene units in the composition not to exceed a specified limit leading to the present invention on the base of this discovery.

Thus, the present invention provides a chemical-amplification positive-working photoresist composition for the formation of a photoresist layer on a substrate surface which comprises (A) a photoacid generating agent, (B) an alkali-insoluble resin capable of being imparted with an increased alkali solubility by interacting with an acid, (C) an alkali-soluble resin and (D) an organic solvent, wherein the component (C) includes (C₁) a copolymer containing at least 80% by mass of hydroxystyrene units or a polyhydroxystyrene with the proviso that the content of the hydroxystyrene copolymer or polyhydroxystyrene (C₁) relative to 100 parts by mass of the total amount of the component (B) and component (C) does not exceed 15 parts by mass.

In the next place, more detailed descriptions are given on the constituents characterizing the present invention.

The photoacid-generating agent used as the component (A) in the inventive composition means a compound capable of generating an acid by irradiation with actinic rays or a radiation and, in the present invention, any one can be used by freely selecting from those heretofore used in chemical-amplification positive-working photoresist compositions as a photoacid generating agent without particular limitations.

Examples of such a compound include triazine compounds represented by the general formula

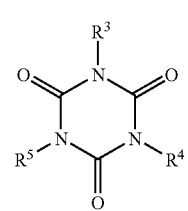

(in the formula, each of R³, R⁴ and R⁵ is an organic group independently from the others) and sulfonyloxyiminoacetonitrile compounds represented by the general formula

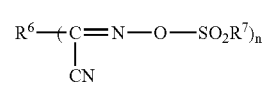

(in the formula, R⁶ is a monovalent to tervalent organic group, R⁷ is a substituted or unsubstituted aliphatic, alicyclic or aromatic hydrocarbon group and n is an integer of 1 to 3).

The organic group denoted by R³, R⁴ and R⁵ in the above-given general formula (I) includes aliphatic, alicyclic or aromatic hydrocarbon groups as well as heterocyclic groups and they can optionally be substituted with one or a plurality of halogen atoms, hydroxyl groups, alkoxy groups, nitro groups and the like.

The aliphatic or alicyclic hydrocarbon groups can be either saturated ones or unsaturated ones. Preferable heterocyclic groups include furyl group, thienyl group, pyrolyl group and the like.

The compounds represented by the general formula (I) can be exemplified by halogen-containing triazine compounds such as 2,4-bis(trichloromethyl)-6-pyperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis(trichloromethyl)-6-(3-bromo-4-methoxy)phenyl-s-triazine, 2,4-bis(trichloromethyl)-6-(2-bromo-4-methoxy)phenyl-s-triazine, 2,4-bis(trichloromethyl)-6-(2-bromo-4-methoxy)styrylphenyl-s-triazine, 2,4-bis(trichloromethyl)-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1, 3,5-triazine, tris(2,3-dibromopropyl)-1,3,5-triazine and the like as well as tris(2,3-dibromopropyl) isocyanurate.

The $R^6$ in the general formula (II) can be exemplified, for example, by aromatic hydrocarbon groups such as phenyl group, and naphthyl group and heterocyclic groups such as furyl group, thienyl group and prolyl group. They optionally have one or a plurality of halogen atoms, alkyl groups, alkoxyl groups, nitro groups and the like as the ring-substituting groups. Further, preferable groups as the $R^7$ include alkyl groups of 1 to 4 carbon atoms such as methyl group, ethyl group, propyl group, isopropyl group, butyl group, tert-butyl group and isobutyl group.

Such a compound is exemplified by, for example, α-(p-toluenesulfonyloxyimino)phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile, α-(ethylsulfonyloxyimino)-1-cyclopentenylacetonitrile and the like and those particularly preferable are the compounds of which n is 1, $R^6$ is a phenyl, methylphenyl or methoxyphenyl group and $R^7$ is a methyl group, such as α-(methylsulfonyloxyimino)-1-phenylacetonitrile, α-(methylsulfonyloxyimino)-1-(4-methylphenyl)acetonitrile, and α-(methylsulfonyloxyimino)-1-(4-methoxyphenyl)acetonitrile.

As the compound having n equal to 2, further, those compounds having a structure shown below are preferred.

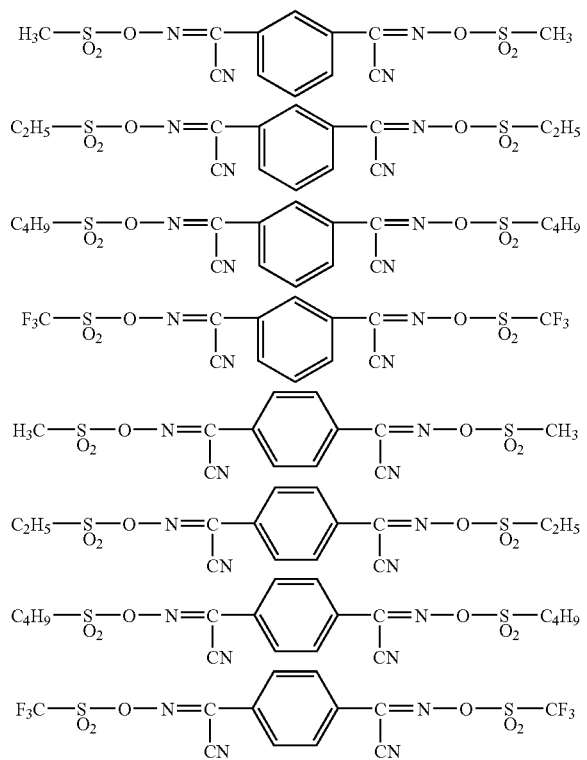

In addition, usable photoacid generating agents include bis(sulfonyl)diazomethane compounds such as bis(p-toluenesulfonyl)diazomethane, bis(1,1-dimethylethylsulfonyl)diazomethane, bis(cyclohexylsulfonyl)diazomethane, bis(2,4-dimethylphenylsulfonyl)diazomethane and the like; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate, dinitrobenzyl carbonate and the like; esters of sulfonic acid such as pyrogallol trimesylate, pyrogallol tritosylate, benzyl tosylate, benzyl sulfonate, (N-methylsulfonyloxy)succinimide, (N-trichloromethylsulfonyloxy)succinimide, (N-phenylsulfonyloxy)maleimide, (N-methylsulfonyloxy)phthalimide and the like; esters of trifluoromethane sulfonic acid such as (N-hydroxy)phthalimide, (N-hydroxy)naphthalimide and the like; onium salts such as diphenyliodonium hexafluorophosphate, (4-methoxyphenyl)phenyliodonium trifluoromethanesulfonate, bis(4-tert-butylphenyl)iodonium trifluoromethanesulfonate, triphenylsulfonium hexafluorophosphate, (4-methoxylphenyl)diphenylsulfonium trifluoromethanesulfonate, (4-tert-butylphenyl)diphenylsulfonium trifluoromethanesulfonate and the like; benzoin tosylates such as benzoin tosylate, α-methylbenzoin tosylate and the like as well as other compounds such as diphenyliodonium salts, triphenylsulfonium salts, phenyldiazonium salts, benzyl carbonates and the like.

These photoacid generating agents as the component (A) can be used either singly or as a combination of two kinds or more.

The compounding amount of the component (A) should be 0.1 to 20 parts by mass or, preferably, 0.2 to 10 parts by mass per 100 parts by mass of the total amount of the components (B) and (C). The sensitivity would be sufficiently high by taking at least 0.1 part by mass while a uniform solution with improved storage stability can be obtained as a trend due to increased solubility in solvents by taking 20 parts by mass or smaller.

As the component (B) in the inventive composition, any one freely selected from among the resins under conventional use as an alkali-insoluble resin capable of being imparted with increased solubility in an alkali solution by interaction with an acid for conventional chemical-amplification positive-working photoresist compositions can be used without particular limitations.

Particularly preferred as the alkali-insoluble resin of the type is a resin consisting of a copolymer containing the monomeric units represented by the general formula (III)

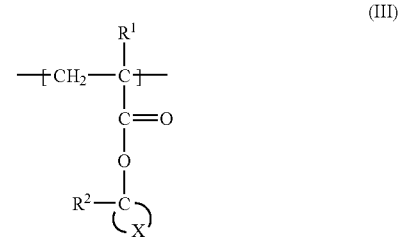

(in the formula, $R^1$ is a hydrogen atom or a methyl group, $R^2$ is an alkyl group having 1 to 5 carbon atoms and X is a divalent hydrocarbon group capable of forming a cyclic structure of 5 to 20 carbon atoms with the carbon atom to which X is bonded).

In the general formula (III) given above, $R^1$ is a hydrogen atom or a methyl group and the alkyl group denoted by $R^2$ can be either linear or branched. $R^2$ is exemplified, for example, by methyl, ethyl, n-propyl, isopropyl, n-butyl, isobutyl, sec-butyl, tert-butyl groups as well as various pentyl groups and the like, among which alkyl groups having 2 to 4 carbon atoms are preferable in respects of the high contrast and good pattern resolution and focusing depth latitude.

In the above-given general formula, X is a divalent hydrocarbon group capable of forming a monocyclic or polycyclic structure of 5 to 20 carbon atoms with the carbon atom to which X is bonded. The monocyclic hydrocarbon ring formed with this X includes cyclopentane, cyclohexane, cycloheptane, cyclooctane and the like.

The polycyclic hydrocarbon rings include dicyclic hydrocarbon rings, tricyclic hydrocarbon rings and tetracyclic hydrocarbon rings and the polycyclic hydrocarbon rings such as adamantine, norbornane, isobornane, tricyclodecane, tetracyclododecane and the like are included.

The hydrocarbon rings having 5 to 20 carbon atoms formed by X together with the carbon atom to which the same is bonded includes, particularly preferably, cyclohexane ring and adamantine ring.

Examples of those structural units represented by the above-given general formula (III) include the structural units expressed by the general formulas

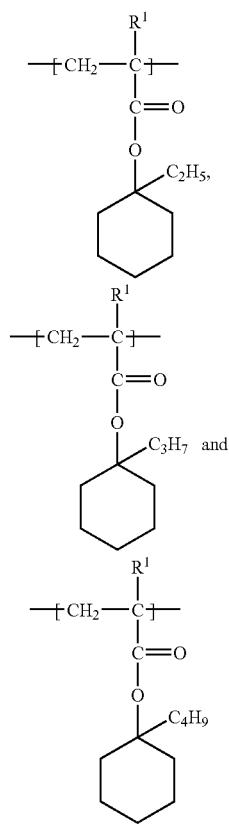

($R^1$ in the above-given formulas has the same meaning as defined before). These structural units either can be used singly or can be used in combination of two kinds or more.

The composition of the present invention can be imparted with an increased solubility change (contrast) in an alkali before and after the exposure to light when the component (B) used contains the structural units represented by the above-given general formula (III).

While the component (B) in the present invention can be a resin of a polymer constituted of the structural units represented by the above-given general formula (III) alone, the component is preferably a resin of a copolymer containing those structural units and the structural units derived from a monomer having an ether linkage. Improvements can be obtained by containing the structural units derived from the monomer having an ether linkage in respects of the adhesion of the alkali-insoluble resin as the component (B) in the development procedure and the resistance against plating solutions.

While these structural units are derived from a monomer having an ether linkage, such a monomer is exemplified by those radical-polymerizable compounds such as, for example, (meth)acrylic acid derivatives having an ether linkage and an ester linkage such as 2-methoxyethyl (meth) acrylate, 2-ethoxyethyl (meth)acrylate, methoxytriethyleneglycol (meth)acrylate, 3-methoxybutyl (meth)acrylate, ethylcarbitol (meth)acrylate, phenoxypolyethyleneglycol (meth)acrylate, methoxypolypropyleneglycol (meth)acrylate, tetrahydrofurfuryl (meth)acrylate and the like. Particularly preferable are 2-methoxyethyl (meth)acrylate, 2-ethoxyethyl (meth)acrylate and methoxytriethyleneglycol (meth)acrylate. These monomers can be used either singly or as a combination of two kinds or more.

In addition to the structural units represented by the above-given general formula (III) and the structural units derived from a monomer having an ether linkage, the component (B) in the composition of the present invention can further contain other structural units with an object to further control the physical and chemical properties of the resin.

Such monomers are exemplified by known radical-polymerizable compounds and anionically polymerizable compounds. For example, the examples include radical-polymerizable compounds such as monocarboxylic acids such as acrylic acid, methacrylic acid, crotonic acid and the like; dicarboxylic acids such as maleic acid, fumaric acid, itaconic acid and the like; methacrylic acid derivatives having a carboxyl group and an ester linkage such as 2-methacryloyloxyethyl succinate, 2-methacryloyloxyethyl maleate, 2-methacryloyloxyethyl phthalate, 2-methacryloyloxyethyl hexahydrophthalate and the like; alkyl esters of (meth)acrylic acid such as methyl (meth)acrylate, ethyl (meth)acrylate, butyl (meth)acrylate and the like; hydroxyalkyl esters of (meth)acrylic acid such as 2-hydroxyethyl (meth)acrylate, 2-hydroxypropyl (meth)acrylate and the like; aryl esters of (meth)acrylic acid such as phenyl (meth)acrylate, benzyl (meth)acrylate and the like; diesters of dicarboxylic acid such as diethyl maleate, dibutyl fumarate and the like; vinyl group-containing aromatic compounds such as styrene, α-methylstyrene, chlorostyrene, chloromethylstyrene, vinyltoluene, hydroxystyrene, α-methylhydroxystyrene, α-ethylhydroxystyrene and the like; vinyl group-containing aliphatic compounds such as vinyl acetate and the like; conjugate diolefins such as butadiene, isoprene and the like; nitrile group-containing polymerizable compounds such as acrylonitrile, methacrylonitrile and the like; chlorine-containing polymerizable compounds such as vinyl chloride, vinylidene chloride and the like; and amide linkage-containing polymerizable compounds such as acrylamide, methacrylamide and the like.

The content of the aforementioned structural units represented by the general formula (III) in the component (B) should be from 10 to 90% by mass or, preferably, from 30 to 70% by mass. When 90% by mass is exceeded, a decrease is caused in the sensitivity while the residual film thickness is decreased when the content is lower than 10% by mass.

The content of the structural units derived from a monomer having an ether linkage in the component (B) should be from 10 to 90% by mass or, preferably, from 30 to 70% by mass. When this proportion exceeds 90% by mass, a decrease is caused in the residual film thickness ratio while, when lower than 10% by mass, a decrease is caused in the adhesion to the substrate in the course of development and in the resistance against plating solutions.

The component (B) should have a mass-average molecular weight by making reference to polystyrenes (referred to hereinbelow as the mass-average molecular weight) of 10000 to 600000 or, preferably, 30000 to 500000 or, more preferably, 50000 to 400000. When the mass-average molecular weight exceeds 600000, a decrease is caused in the peelability while, when smaller than 10000, risks are resulted because the strength of the resist film cannot be sufficiently high along with expansion of the profile and occurrence of cracks in the course of plating. The cracking resistance is also decreased when the mass-average molecular weight is smaller than 230000.

Besides, it is preferable that the component (B) is a resin having the degree of dispersion not smaller than 1.05. The degree of dispersion implied here is the value of the mass-average molecular weight divided by the number-average molecular weight. When the degree of dispersion is smaller than 1.05, the resistance against stress by plating is decreased resulting in bulging of the metal layer obtained by the plating treatment.

The compounding amount of the component (B) is from 5 to 95 parts by mass or, preferably, from 10 to 90 parts by mass per 100 parts by mass of the total amount of the component (B) and component (C). The reason therefor is that the risk of occurrence of cracks in plating is decreased by taking 5 parts by mass or larger and the sensitivity is improved when the amount does not exceed 95 parts by mass.

In the composition of the present invention, it is essential that an alkali-soluble resin is contained as the component (C). This alkali-soluble resin plays a role to regulate the coating adaptability and developing velocity of the composition.

As the component (C), ($C_1$) a polyhydroxystyrene or a copolymer containing at least 80% by mass of the hydroxystyrene units can be used. The hydroxystyrene here implied includes not only the hydroxystyrenes such as p-hydroxystyrene and the like but also α-methyl hydroxystyrene, α-ethyl hydroxystyrene and the like.

The comonomers to be copolymerized to give a copolymer containing at least 80% by mass of the hydroxystyrene units preferably include; for example, styrene; styrene derivatives such as chlorostyrene, chloromethylstyrene, vinyl toluene, α-methylstyrene, β-methylstyrene, p-methoxystyrene and the like; acrylamides such as diacetone acrylamide and the like; acrylonitrile; ethers of vinyl alcohol such as vinyl n-butyl ether and the like; (meth)acrylic acid-based monomers such as alkyl (meth)acrylates, tetrahydrofurfuryl (meth)acrylate, dimethylaminoethyl (meth)acrylate, glysidyl (meth)acrylate, 2,2,2-trifluoroethyl (meth)acrylate, (meth)acrylic acid, α-bromo(meth)acrylic acid, β-furyl(meth)acrylic acid, β-styryl(meth)acrylic acid and the like; maleic acid based monomers such as maleic acid, maleic acid anhydride, monomethyl maleate and the like. Moreover, fumaric acid, cinnamic acid, α-cyano cinnamic acid, itaconic acid, crotonic acid and propiolic acid can be named. From the standpoint of copolymerizability and coating behavior, it is preferable to use a styrene compound such as styrene, chloromethylstyrene, vinyl toluene, α-methylstyrene, p-methoxystyrene and the like.

It is essential in the inventive composition that the copolymer containing at least 80% by mass of the hydroxystyrene units or the polyhydroxystyrene ($C_1$) is controlled not to exceed 15 parts by mass relative to 100 parts by mass of the total mass amount of the resinous ingredient in the inventive composition or, namely, the total of the component (B) and the component (C). When the amount of ($C_1$) exceeds 15 parts by mass, a resist pattern having good fidelity cannot be obtained by development due to deficiency in solubility. The lower limit of the amount of ($C_1$) is, though not particularly limitative, usually, 1 part by mass or, preferably, 5 parts by mass. In the present invention, it is preferable according to need that a novolac resin ($C_2$) is admixed in the component (C). The novolac resin is a resin obtained by the addition condensation reaction conducted between a phenolic compound such as phenol, o-cresol, m-cresol, p-cresol, o-ethylphenol, m-ethylphenol, p-ethylphenol, 2,3-xylenol, 2,4-xylenol, 2,5-xylenol and the like and an aldehyde compound such as formaldehyde, furfural, benzaldehyde, acetaldehyde and the like in the presence of an acid such as hydrochloric acid, formic acid and oxalic acid. Compounding of a novolac resin has an effect to facilitate control of the coating behavior and the development velocity.

In addition to the components (A), (B) and (C), it is optional according to need that the composition of the present invention is admixed, as an acid diffusion controller, a nitrogen-containing compound, an organic carboxylic acid or an oxoacid of phosphorus or a derivative thereof.

The above-mentioned nitrogen-containing compound includes, for example, trimethylamine, diethylamine, triethylamine, di-n-propylamine, tri-n-propylamine, tribenzlylamine, diethanolamine, triethanolamine, n-hexylamine, n-heptylamine, n-octylamine, n-nonylamine, ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, formamide, N-methylformamide, N,N-dimethylformamide, acetamide, N-methylacetamide, N,N-dimethylacetamide, propionamide, benzamide, pyrrolidone, N-methylpyrrolidone, methylurea, 1,1-dimethylurea, 1,3-dimethylurea, 1,1,3,3-tetramethylurea, 1,3-diphenylurea, imidazol, benzimidazol, 4-methylimidazol, 8-oxyquinoline, acridine, purine, pyrrolidine, piperidine, 2,4,6-tri(2-pyridyl)-S-triazine, morpholine, 4-methylmorpholine, piperazine, 1,4-dimethylpiperazine, 1,4-diazabicyclo[2.2.2]octane and the like. Among them, alkanolamines such as triethanolamine are particularly preferable.

The above named compounds can be used either singly or as a combination of two kinds or more. They are preferably used in an amount not exceeding, usually, 5 parts by mass or, in particular, 3 parts by mass per 100 parts by mass of the total amount of the components (B) and (C).

The above-mentioned organic carboxylic acid includes malonic acid, citric acid, malic acid, succinic acid, benzoic acid, salicylic acid and the like, of which salicylic acid is preferred.

The oxoacid of phosphorus or a derivative thereof is exemplified by phosphoric acid and derivatives, i.e. esters, thereof including phosphoric acid, di-n-butyl phosphate, diphenyl phosphate and the like; phosphonic acid and derivatives thereof such as esters including phosphonic acid, dimethyl phosphonate, di-n-butyl phosphonate, phenylphosphonic acid, diphenyl phosphonate, dibenzyl phosphonate and the like; and phosphinic acid and derivatives, i.e. esters, thereof including phosphinic acid, phenylphosphinic acid and the like, of which phosphonic acid is particularly preferable.

These compounds can be used either singly or as a combination of two kinds or more. They are used in an amount not exceeding 5 parts by mass or, in particular, not exceeding 3 parts by mass per 100 parts by mass of the total amount of the components (B) and (C).

The composition of the present invention is prepared by dissolving the components (A), (B) and (C) as well as the desired ingredients in an organic solvent as the component (D).

Examples of suitable organic solvents include ketones such as acetone, methyl ethyl ketone, cyclohexanone, methyl isoamyl ketone, 2-heptanone and the like; polyhydric alcohols and derivatives thereof such as ethyleneglycol, ethyleneglycol monoacetate, diethyleneglycol, diethyleneglycol monoacetate, propyleneglycol, propyleneglycol monoacetate, dipropyleneglycol and dipropyleneglycol monoacetate as well as monomethyl, monoethyl, monopropyl, monobutyl and monophenyl ether compounds thereof; cyclic ethers such as dioxane; and ester compounds such as methyl lactate, ethyl lactate, methyl acetate, ethyl acetate, butyl acetate, methyl pyruvate, ethyl pyruvate, methyl methoxypropionate and ethyl ethoxypropionate and the like. These organic solvents can be used either singly or as a mixture of two kinds or more. It is particularly preferable to use propyleneglycol methyl ether acetate or a mixture thereof with other organic solvents.

The amount of these solvents to be used is preferably such that the chemical-amplification positive-working photoresist composition prepared therewith has a solid content in the range from 30 to 65% by mass. When the solid content of the composition is too low, it is difficult to obtain a large-thickness film suitable for the preparation of connecting terminals while, when the solid content is too high, the composition would have an unduly decreased flowability to cause difficulties in handling in addition to the problem that no uniformity can be accomplished in the coating works with the composition.

It is optional according to need that the chemical-amplification positive-working photoresist composition of the present invention is further admixed with other additives having miscibility such as auxiliary resins to improve the film characteristics of the resist film, plasticizers, adhesion aids, coloring agents, stabilizers, surface active agents and others under conventional use within a range not to decrease the inherent properties of the composition.

The composition of the present invention is a chemical-amplification positive-working photoresist composition for the formation of a photoresist layer having a thickness of, in particular, 10 to 150 µm or, preferably, 20 to 120 µm on a substrate.

The substrate material used here can be any one freely selected from among the substrate materials used as a base plate in the manufacture of electronic devices without particular limitations. Such a substrate material includes, besides glass base plates and silicon wafers, wafers having a coating layer of a metal such as titanium, tantalum, tungsten, palladium, copper, chromium, iron, aluminum and the like as well as alloys thereof and nitrides, silicides and carbides thereof, of which silicon wafers are the most suitable. These substrates can be provided on the surface with a circuit wiring pattern formed with copper, chromium, aluminum, nickel, gold, silver, platinum and the like.

A large-thickness resist layer of the inventive composition can be formed on such a substrate material according to a conventional procedure by coating the substrate surface with the composition in such a coating amount to give an as-dried film thickness of 10 to 150 µm or, preferably, 20 to 120 µm followed by removal of the solvent by heating. The coating method here undertaken can be any one conventional in use for the formation of a planar coating layer including spin-coating method, slit coating method, roller coating method, screen printing method, applicator method and others. Though dependent on the formulation of the composition used, desired film thickness of the coating layer and other factors, sufficient drying can be accomplished with the conditions of heating undertaken after coating including a temperature of 70 to 150° C. or, preferably, 80 to 140° C. and a heating time of 2 to 60 minutes.

In the next place, formation of a patterned resist layer by using the substrate thus provided with a large-thickness resist layer formed with the inventive resist composition can be accomplished by a process in which the resist layer is irradiated with actinic rays or radiation through a photomask of a particular pattern to effect image-forming light exposure. Ultraviolet light or visible light having a wavelength of 300 to 500 nm is preferred as the actinic rays or radiation but, besides, near-ultraviolet light, X-rays, electron beams, various kinds of ion beams and others can also be used. Suitable sources of the actinic rays and radiations include low-pressure mercury lamps, high-pressure mercury lamps, ultrahigh-pressure mercury lamps, metal halide lamps, argon gas lasers and the like. The irradiation dose required in this case is usually 100 to 10000 mJ/cm$^2$ when a high-pressure mercury lamp is used though dependent on the types of the light source used, formulation of the resist composition, thickness of the desired resist layer and other factors.

A patterned resist layer is then formed by subjecting the large-thickness resist layer in the light-exposed areas by means of the above-described image-forming light exposure to a development treatment with an alkaline solution by utilizing the alkali-solubility of the resist layer. The alkaline solution can be an aqueous solution of an alkaline compound such as, for example, sodium hydroxide, potassium hydroxide, sodium carbonate, sodium silicate, sodium methasilicate, ammonia water, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, 1,8-diazabicyclo[5.4.0]-7-undecene, 1,5-diazabicyclo[4.3.0]-5-nonane and the like, which can optionally be admixed according to need with a water-miscible organic solvent such as methanol, ethanol and the like and a surface active agent.

Though dependent on the types and compounding proportion of the respective components in the resist composition and the thickness of the resist layer as dried, the development time is usually from 1 to 30 minutes and the method of development can be any one selected from the liquid-mounting method, dipping method, puddle method, spray-development method and others. The development treatment thus conducted is followed by rinse of the developed resist layer in a running water stream taking 30 to 90 seconds and then by drying using an air gun or a drying oven.

It is now possible to form a connecting terminal such as metal posts and bumps in the resist-free areas, i.e. the areas from which the resist layer has been removed with the alkaline developer solution, of the resist pattern obtained in the above-described manner by embedding conductive members such as metals by conducting, for example, plating. Though not particularly limitative, various known methods can be undertaken for the plating treatment by using a plating liquid which can be a solution for solder plating, copper plating, gold plating, or nickel plating as the preferable examples.

The remaining resist pattern is finally removed by using a remover solution and the like according to a conventional procedure. By repeating formation of a resist pattern and plating treatment in this way, an electronic base material for mounting of a multiple-pin thin film can be manufactured.

In the following, the best mode to practice the present invention is described in further detail by way of Examples which, however, never limit the scope of the invention in any way.

In the Examples described below, evaluation was undertaken for the workability of the photoresist compositions and the properties of the coating films by the procedures given below.

(1) Coating Adaptability

A 5-inch silicon wafer having a sputtered layer of gold, hereinafter referred to as a gold substrate, was coated on a spinner with the composition in a coating thickness of 100 µm followed by heating in an oven at 120° C. for 60 minutes. The thus formed dried coating film was examined under an optical microscope to record the condition of the coating film in three rates A, B and C according to the following criteria.

A: The coating film was uniform with absolutely no noticeable unevenness.
B: The coating film was nearly complete at an acceptable level, though with a small number of sporadic minute spots of unevenness.
C: The coating film was non-uniform portionwise with sporadic minute spots of unevenness all over the surface.

(2) Developability

A gold-sputtered 5-inch silicon wafer was coated with the photoresist composition by using a spinner rotating at 1800 rpm for 25 seconds followed by prebaking for 6 minutes on a hot plate at 110° C. to form a resist film of 20 µm thickness. The resist film was exposed to ultraviolet light in an intensity of 200, 400, 800 or 1000 mJ/cm$^2$ through a photomask of 20 µm line-and-space pattern for resolution measurement by using a stepper (Model NSR-2005i10D, a product by Nikon Co.) followed by a heat treatment at 74° C. for 5 minutes and then a development treatment by using a developer solution (P-7G, PMER Series, a product by Tokyo Ohka Kogyo Co.). Evaluation of the developability was undertaken in terms of the minimum light-exposure dose required for accomplishment of this development. A smaller minimum exposure dose was taken as to correspond to better developability.

(3) Resistance Against Plating Solution

A substrate bearing the patterned resist layer formed in (2) above was subjected to an ashing treatment with oxygen plasma and then dipped in a sulfurous acid gold-plating solution kept at 65° C. for 40 minutes followed by rinse in a running stream of water to prepare a test specimen which was examined under an optical microscope for the condition of the patterned resist film to record the results as Good when no changes could be detected and as No Good when occurrence of cracks, bulging or falling was detected in the resist film.

(4) Removability

The resist pattern formed in (2) above was dipped in a remover solution (Stripper 104, a product by Tokyo Ohka Kogyo Co.) kept at 23° C. or 70° C. for 20 minutes followed by rinse with isopropyl alcohol and the condition of the substrate surface was examined under an optical microscope of 50 magnifications to count the number of the unremoved debris fragments and the results were recorded as A, B and C as a measure of the removability according to the following criteria.

A: none
B: 1 or 2 fragments per cm$^2$
C: 3 fragments per cm$^2$

Reference Example 1

By using propyleneglycol methyl ether acetate as the reaction solvent and using 2,2'-azobisisobutyronitrile as the polymerization initiator, copolymerization was carried out with 1-ethylcyclohexyl methacrylate, 2-ethoxyethyl acrylate and styrene in a mass proportion of 2:6:2 to prepare an alkali-insoluble copolymeric resin (B-1) having a mass-average molecular weight of 200000 and capable of being imparted with increased solubility in alkali by interaction with an acid.

Reference Example 2

An alkali-insoluble copolymeric resin (B-2) having a mass-average molecular weight of 200000 and capable of being imparted with increased solubility in alkali by interaction with an acid was prepared in the same manner as in Reference Example 1 excepting for the use of 1-ethylcyclohexyl methacrylate and 2-ethoxyethyl acrylate in a mass proportion of 2:8 as the comonomers.

Reference Example 3

An alkali-insoluble copolymeric resin (B-3) having a mass-average molecular weight of 200000 and capable of being imparted with increased solubility in alkali by interaction with an acid was prepared in the same manner as in Reference Example 1 excepting for the use of adamantyl acrylate and 2-ethoxyethyl acrylate as the comonomers in a mass proportion of 2:8.

Reference Example 4

An alkali-insoluble copolymeric resin (B-4) having a mass-average molecular weight of 200000 and capable of being imparted with increased solubility in alkali was prepared in the same manner as in Reference Example 1 excepting for the use of adamantyl acrylate and 2-ethoxyethyl acrylate as the comonomers in a mass proportion of 5:5.

Reference Example 5

An alkali-insoluble copolymeric resin (B-5) having a mass-average molecular weight of 200000 and capable of being imparted with increased solubility in alkali by interaction with an acid was prepared in the same manner as in Reference Example 1 excepting for the use of 1-ethylcyclohexyl methacrylate and 2-ethoxyethyl acrylate as the comonomers in a mass proportion of 5:5.

Reference Example 6

A novolac resin having a mass-average molecular weight of 15000 was prepared by conducting a condensation reaction between a 60:40 mass proportion mixture of m-cresol and p-cresol and formalin in the presence of oxalic acid catalyst according to a conventional method to obtain a cresol novolac resin followed by removal of the low molecular weight fractions.

Example 1

90 parts by mass of the resin (B-1) capable of being imparted with increased solubility in alkali by interaction with an acid as obtained in Reference Example 1 and 10 parts by mass of a polyhydroxystyrene were dissolved in propyleneglycol monomethyl ether acetate to obtain a solution of a 50% by mass solid content, which was admixed with 1 part by mass of (5-propylenesulfonyloxyimino-5H-thiophen-2-ylidene)-(2-methylphenyl) acetonitrile as a photoacid generating agent to be uniformly dissolved followed by filtration through a membrane filter of 1 µm pore diameter to prepare a chemical-amplification positive-working photoresist composition. Properties thereof are shown in Table 1.

Example 2

A chemical-amplification positive-working photoresist composition was prepared in the same manner as in Example 1 excepting for the replacement of the polyhydroxystyrene in Example 1 with 10 parts by mass of a copolymer consisting of 90% by mass of hydroxystyrene units and 10% by mass of styrene units. The properties thereof are shown in Table 1.

hydroxystyrene units different each from the others to a mixture of 50 parts by mass of the alkali-insoluble resin (B-2) obtained in Reference Example 2 and 40 parts by mass of the novolac resin obtained in Reference Example 6. The properties of these compositions are shown in Table 1.

As is clear from Table 1, a decrease is noted in the developability and removability when the content of the hydroxystyrene units in the component $(C_1)$ is lower than 80% by mass although little influences are noted on the coating adaptability and resistance against plating solutions.

TABLE 1

| | Content of hydroxystyrene units in component $(C_1)$, % by mass | Mass proportion of component $(C_1)$ per 100 parts by mass of total amount of components (B) and (C), parts by mass | Properties | | | Removability | |
|---|---|---|---|---|---|---|---|
| | | | Coating adaptability | Developability, mJ/cm$^2$ | Resistance against plating solutions | 23° C. | 70° C. |
| Example 1 | 100 | 10 | B | 400 | Good | A | A |
| Example 2 | 90 | 10 | B | 400 | Good | A | A |
| Example 3 | 100 | 10 | A | 200 | Good | A | A |
| Example 4 | 100 | 13 | A | 200 | Good | A | A |
| Example 5 | 90 | 10 | A | 200 | Good | A | A |
| Example 6 | 80 | 10 | A | 400 | Good | A | A |
| Comparative Example 1 | 100 | 17 | C | 200 | Good | A | A |
| Comparative Example 2 | 70 | 10 | A | 600 | Good | B | A |
| Comparative Example 3 | 50 | 10 | A | 1000 | Good | C | A |

Examples 3 and 4 and Comparative Example 1

A chemical-amplification positive-working photoresist composition was prepared in each of these examples excepting for the addition of 10 parts by mass, 13 parts by mass or 19 parts by mass, respectively, of a polyhydroxystyrene to a mixture of 50 parts by mass of the alkali-insoluble resin (B-2) obtained in Reference Example 2 and 40 parts by mass of the novolac resin obtained in Reference Example 6. Properties of these compositions are shown in Table 1.

As is clear from Table 1, a great decrease is noted in the coating adaptability of the composition when the mass proportion of the component $(C_1)$ exceeds 15 parts by mass per 100 parts by mass of the total amount of the component (B) and component (C) although little influences are noted in the developability, resistance against plating solutions and removability.

Example 7

A chemical-amplification positive-working photoresist composition was prepared in the same manner as in Example 2 excepting for the replacement of the photoacid generating agent with the same amount of 1,3-bis(butylsulfonyloxyimino-α-cyanomethyl)benzene. The properties of this composition are shown in Table 2.

Examples 8 to 10

A chemical-amplification positive-working photoresist composition was prepared in each of these Examples in the same manner as in Example 2 excepting for the use of each 40 parts by mass of the novolac resin obtained in Reference Example 6 and 50 parts by mass each of the resin (B-3) obtained in Reference Example 3, the resin (B-4) obtained in Reference Example 4 or (B-5) obtained in Reference Example 5, respectively, as the alkali-insoluble resin. The properties of these compositions are shown in Table 2.

TABLE 2

| | | | Properties | | | Removability | |
|---|---|---|---|---|---|---|---|
| Example | Component (A)* | Component (B) | Coating adaptability | Developablility, mJ/cm$^2$ | Resistance against plating solutions | 23° C. | 70° C. |
| 7 | A-2 | B-2 | A | 200 | Good | A | A |
| 8 | A-1 | B-3 | A | 200 | Good | A | A |
| 9 | A-1 | B-4 | A | 400 | Good | A | A |
| 10 | A-1 | B-5 | A | 400 | Good | A | A |

*A-1: (5-propylenesulfonyloxyimino-5H-thiophen-2-ylidene)-(2-methylphenyl)acetonitrile
A-2: 1,3-bis(butylsulfonyloxyimino-α-cyanomethyl)benzene Examples 5 and 6 and Comparative Examples 2 and 3

A chemical-amplification positive-working photoresist composition was prepared in each of these examples in the same manner as in Example 1 excepting for the addition of 10 parts by mass of the copolymeric component $(C_1)$ of hydroxystyrene and styrene having a mass proportion of the As is understood from Table 2, a chemical-amplification positive-working photoresist composition having excellent properties can be obtained insofar as the requirements are satisfied that the content of the hydroxystyrene units in the component $(C_1)$ is at least 80% by mass and that the mass proportion of the component $(C_1)$ per 100 parts by mass of the total amount of the component (B) and component (C) does not exceed 15 parts by mass.

INDUSTRIAL UTILIZABILITY

Provided according to the present invention is a chemical-amplification positive-working photoresist composition suitable for the formation of a photoresist layer having a film thickness of 10 to 150 μm exhibiting good coating adaptability and removability with a high development velocity, capable of giving a resist pattern with high fidelity, and being free from the troubles of dissolution in the unexposed areas during development.

Accordingly, the chemical-amplification positive-working photoresist composition of the present invention is useful as a material in the manufacture of electronic devices involving multiple-pin thin-film mounting.

The invention claimed is:

1. A chemical-amplification positive-working photoresist composition for the formation of a photoresist layer on a substrate surface which comprises:
(A) a photoacid generating agent; (B) an alkali-insoluble resin capable of being imparted with an increased alkali solubility by interacting with an acid; (C) an alkali-soluble resin; and (D) an organic solvent,
wherein the component (B) is a resin containing the monomeric units represented by the following formula:

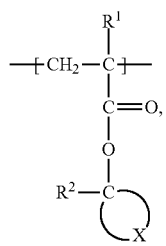

wherein $R^1$ is a hydrogen atom or a methyl group, $R^2$ is an alkyl group having 1 to 5 carbon atoms and X is a divalent hydrocarbon group to form a cyclic structure of 5 to 20 carbon atom members including the carbon atom to which the group denoted by X is bonded, and
wherein the component (C) includes ($C_1$) a copolymer of hydroxystyrene and styrene, and contains at least 80% by mass of hydroxystyrene units,
with the proviso that the content of the component ($C_1$) relative to 100 parts by mass of the total amount of the components (B) and (C) does not exceed 15 parts by mass.

2. The chemical-amplification positive-working photoresist composition according to claim 1, wherein the component (C) is a combination of the component ($C_1$) and ($C_2$) a novolac resin.

3. The chemical-amplification positive-working photoresist composition according to claim 1, wherein the component (D) is propyleneglycol methyl ether acetate or a mixture thereof with another organic solvent.

4. The chemical-amplification positive-working photoresist composition according to claim 1, wherein the component (B) has a mass-average molecular weight in the range of 10,000-600,000.

5. The chemical-amplification positive-working photoresist composition according to claim 1, wherein the content of the component ($C_1$) relative to 100 parts by mass of the total amount of the components (B) and (C) does not exceed 10 parts by mass.

* * * * *